United States Patent [19]

Kaneko et al.

[11] Patent Number: 5,304,558

[45] Date of Patent: Apr. 19, 1994

[54] DIPHENYLMETHYL PIPERAZINE DERIVATIVES

[75] Inventors: Noboru Kaneko; Makoto Takeishi, both of Tokyo; Tatsushi Oosawa, Gunma; Kouji Akimoto, Gunma; Hideo Oota, Gunma; Tatsuo Nakajima, Gunma, all of Japan

[73] Assignee: Kirin Brewery Co., Ltd., Tokyo, Japan

[21] Appl. No.: 958,366

[22] PCT Filed: Jul. 10, 1991

[86] PCT No.: PCT/JP91/00924

§ 371 Date: Mar. 2, 1993

§ 102(e) Date: Mar. 2, 1993

[87] PCT Pub. No.: WO92/00962

PCT Pub. Date: Jan. 23, 1992

[30] Foreign Application Priority Data

Jul. 10, 1990 [JP] Japan .................. 2-182095

[51] Int. Cl.$^5$ .................. A61K 31/495; C07D 211/52; C07D 217/04; C07D 401/00
[52] U.S. Cl. .................. 514/253; 514/252; 544/360; 544/361; 544/363
[58] Field of Search .................. 544/363, 360, 361; 514/252, 253; A61K 31/495

[56] References Cited

U.S. PATENT DOCUMENTS 4,832,934 5/1983 Teraji et al. .................. 514/253

FOREIGN PATENT DOCUMENTS 10398 4/1980 European Pat. Off. .
192381 8/1987 Japan .
2186573 2/1987 United Kingdom .

Primary Examiner—Cecilia Tsang

Attorney, Agent, or Firm—Scully, Scott, Murphy & Presser

[57] ABSTRACT

Novel diphenylmethyl piperazine derivatives of this invention have a chemical structure represented by the following Formula [I]:

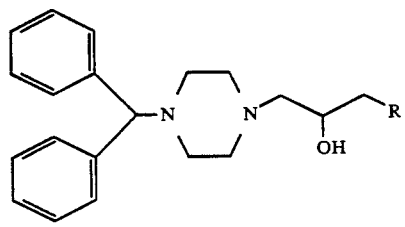

wherein R represents

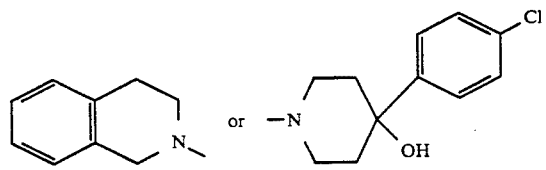

The compounds have an effect of inhibiting the overcontraction and overextension of the myocardium without being accompanied by a myocardium-inhibiting effect. By using the novel diphenylmethyl piperazine derivatives as an effective ingredient, it is possible to obtain a myocardial necrosis inhibitor which can protect against myocardial necrosis, and a drug for the treatment and prevention of acute myocardial infarction.

15 Claims, No Drawings

DIPHENYLMETHYL PIPERAZINE DERIVATIVES

TECHNICAL FIELD

This invention relates to novel diphenylmethyl piperazine derivatives, in particular novel diphenylmethyl piperazine derivatives having an effect of inhibiting overcontraction and overextension of the myocardium and protecting against myocardial necrosis without being accompanied by a cardiodepressant effect.

In addition, this invention relates to drugs containing the aforementioned novel diphenylmethyl piperazine derivatives as an effective ingredient which work on the circulatory system, in particular, drugs containing the novel diphenylmethyl piperazine derivatives as an effective ingredient which inhibit myocardial necrosis and which inhibit overcontraction and overextension of myocardium and protect against myocardial necrosis without being accompanied by a cardiodepressant effect, and drugs containing the same for treatment and prevention of acute myocardial infarction.

BACKGROUND ART

The recent increase in the average age of the population has been accompanied by an increase in circulatory diseases, such as hypertension, angina and myocardial infarction. In particular, there have been many sudden occurrences of acute myocardial infarction with a high mortality rate. Hitherto, the cause of this acute myocardial infarction has been attributed to obstruction, by thrombus or coronary spasm, of the coronary antery which supplies nutrition to the heart. Recently, however, Kaneko et al. have proposed a new mechanism for acute myocardial infarction, according to which the myocardia of myocardial infarction patients exhibit two forms of necrosis, Static cell death (SD) and Kinetic cell death (KD), with KD being the main cause of acute myocardial infarction. (Journal of Tokyo Women's Medical College, 52, 1443, 1982). In addition, Kaneko et al. have reported using a rabbit to create a model of an acute myocardial infarction caused by KD, and using calcium antagonists to inhibit the symptoms thereof (refer to Japanese Patent Application No. Sho 61-40651). Moreover, they have recently succeeded in creating a model of an acute myocardial infarction caused by KD in a Langendorff in vitro system using an isolated rat heart, and using this model they have found that some Ca antagonists have a KD-inhibiting effect similar to that found in the in vivo system. However, some of these Ca antagonists have a strong cardiodepressant effect, and it was thought desirable to develop compounds having a weak cardiodepressant effect, and a strong KD-inhibiting effect.

DISCLOSURE OF THE INVENTION

It is an object of this invention to provide compounds having the above-mentioned KD-inhibiting effect without being accompanied by a cardiodepressant effect, and to provide drugs containing the compounds as an effective ingredient for inhibition of myocardial necrosis and treatment and prevention of acute myocardial infarction.

In addition, it is an object of this invention to provide not only novel diphenylmethyl piperazine derivatives having a KD-inhibiting effect without any accompanying cardiodepressant effect, particularly novel diphenylmethyl piperazine derivatives having specific substituent groups and pharmaceutically acceptable salts thereof, but also to provide drugs for the inhibition of myocardial necrosis and for the treatment and prevention of acute myocardial infarction in which the above novel diphenylmethyl piperazine derivatives having specific substituent groups and pharmaceutically acceptable salts thereof are contained as effective ingredient.

Namely, the compounds of this invention are diphenylmethyl piperazine derivatives having a chemical structure represented by the following Formula [I]:

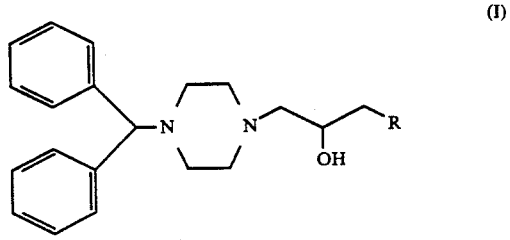

wherein R represents

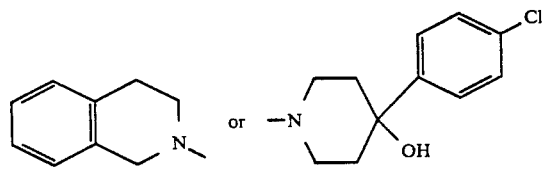

or pharmaceutically acceptable salts thereof.

Moreover, the drugs of this invention for the inhibition of myocardial necrosis and for the treatment and prevention of acute myocardial infarction contain as an effective ingredient one or more of the diphenylmethyl piperazine derivatives having a chemical structure represented by Formula [I] above or pharmaceutically acceptable salts thereof.

The novel diphenylmethyl piperazine derivatives of this invention have a strong myocardial necrosis-inhibiting effect without being accompanied by a cardiodepressant effect, and can be used as an excellent inhibitor of myocardial necrosis and an excellent drug for the treatment and prevention of acute myocardial infarction. Consequently, this invention provides an excellent inhibitor of myocardial necrosis and an excellent drug for the treatment and prevention of acute myocardial infarction.

The ability to produce a strong myocardial necrosis-inhibiting effect without being accompanied by a cardiodepressant effect is a new property discovered in the novel diphenylmethyl piperazine derivatives of this invention.

As can be seen from Formula [I]:

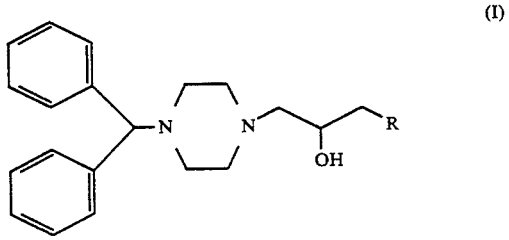

wherein R represents

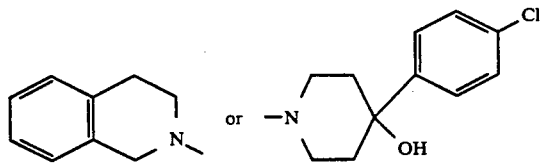

the compound of this invention has basic nitrogen atoms and it is thus possible to form an acid addition salt at this site. The acid used to form an acid addition salt should be selected from pharmaceutically acceptable acids. Consequently, pharmaceutically acceptable salts of the compound shown in Formula [I] also fall within the scope of the compounds in this invention. Salts can include, for sulfate, nitrate, phosphate or the like and a organic acid salts such as citrate, maleate, fumarate, adipate, benzoate, succinate, acetate, tartrate, malate or the like.

The diphenylmethyl piperazine derivatives of Formula [I] of this invention and pharmaceutically acceptable salts thereof can be prepared according to various routes; for example, by following the reaction scheme of Route (A) or (B), provided that R in the reaction formula is as defined in Formula [I] of this invention.

Route (A): The preparation process is as follows.

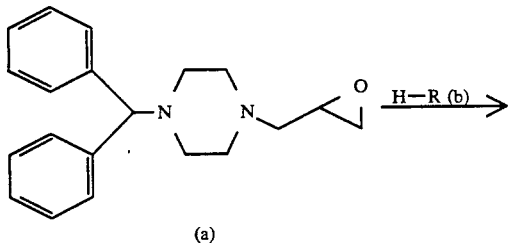

In the above Route (A), the amine compound of Formula (b) is as follows.

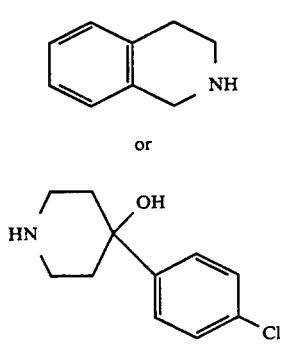

In the preparation process according to Route (A), 1-(diphenylmethyl)-4-[1-(2,3-epoxy)propyl]piperazine is used as a raw epoxide compound (Formula (a)) and tetrahydroisoquinoline or 1-(4-chlorophenyl-4-hydroxy) piperidine is used as a raw amine compound (Formula (b)).

In the preparation process according to Route (A), the epoxide compound, 1-(diphenylmethyl)-4-[1-(2,3-epoxy)propyl]piperazine (formula (a)), is heated with the amine compound, 1,2,3,4-tetrahydroisoquinoline or [4-(4-chlorophenyl)-4-hydroxy]piperidine, in o-dichlorobenzene at reflux for 1 to 4 hours to give the compound of Formula [I].

In the preparation process according to Route (A), if 1,2,3,4-tetrahydroisoquinoline is used as the amine compound of Formula (b), the Formula [I] compound thus obtained is 1-[2-(1,2,3,4-tetrahydro)isoquinolinyl]-3-[1-(4-diphenylmethyl)piperazinyl]-2-propanol.

Furthermore, in the preparation process according to Route (A), if 4-(4-chlorophenyl)-4-hydroxypiperidine is used as the amine compound of Formula (b), the Formula [I] compound thus obtained is 1-[1-(4-diphenylmethyl) piperazinyl]-3-[1-[4-(4-chlorophenyl)-4-hydroxy]piperidinyl]-2-propanol.

In both the above cases, the compounds of Formula [I] which are obtained by the preparation process according the Route (A) can be isolated and purified by conventional methods.

In the preparation process according to Route (A), the starting material of Formula (a) can be prepared by conventional methods relating to preparation of epoxide compounds.

The typical routes for preparing the material of Formula (a) are described in detail in the following experimental examples. The basic reaction is as follows.

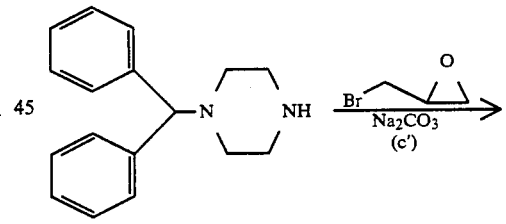

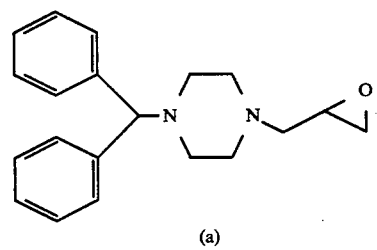

In the above reaction scheme, 1-(diphenylmethyl) piperazine (Formula (c)) is reacted with a reactant, epibromohydrin (Formula (c')) in the presence of sodium carbonate in an inert solvent to give the compound of Formula (a).

Route (B): The preparation process is as follows.

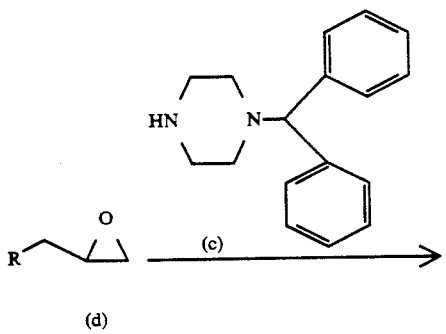

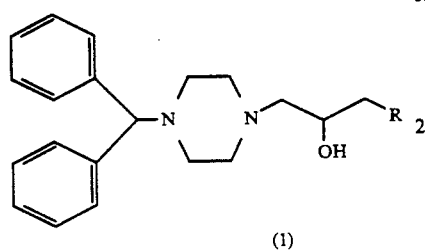

In the preparation process according to Route (B), an epoxide compound of Formula (d) is heated with diphenylmethyl piperazine of Formula (c) in o-dichlorobenzene at reflux for 1 to 4 hrs, to give the compound of Formula [I]. The reaction product can be isolated and purified by conventional methods as mentioned above.

In the preparation process according to Route (B), if R in the epoxide compound is 1,2,3,4-tetrahydroisoquinolinyl group, the epoxide compound is 2-[1-(2,3-epoxy)propyl]-1,2,3,4-tetrahydroisoquinoline and the reaction product thus obtained is 1-[2-(1,2,3,4-tetrahydro)isoquinolinyl]-3-[1-(4-diphenylmethyl) piperazinyl]-2-propanol. Also, in the preparation process according to Route (B), if R in the epoxide compound is 1-[4-(4-chlorophenyl)-4-hydroxy]piperidinyl group, the epoxide compound is 1-[1-(2,3-epoxy)-propyl]-4-(4-chlorophenyl)-4-hydroxypiperidine and the reaction product thus obtained is 1-[1-(4-diphenylmethyl) piperazinyl-3-[1-[4-(4-chlorophenyl)-4-hydroxy]piperidinyl] propanol.

The starting material of Formula (d) can be synthesized in the same manner as that of Formula (a) in Route (A).

The diphenylmethyl piperazine derivatives thus obtained can be converted by conventional methods into the form of the various salts mentioned above.

The diphenylmethyl piperazine derivatives of Formula [I] of this invention and the pharmaceutically acceptable salts have a KD-inhibiting effect and can be useful as a drug for curing a circulatory disease. Concretely, the derivatives are useful as drugs for anti-myocardial necrosis, as drugs for inhibition and prevention of myocardial necrosis and as drugs for treatment and prevention of acute myocardial infarction.

The inhibitor for the myocardial necrosis and the drug for treatment and prevention of acute myocardial infarction of this invention contain as an effective ingredient one or more of the compounds of the Formula [I] and the pharmaceutically acceptable salts thereof.

In the case that the compounds of this invention are used as drugs for inhibition or prevention of myocardial necrosis or drugs for treatment or prevention of acute myocardial infarction, the dosage thereof varies depending on the degree of disease, the patient's weight, method of administration or the like and is not particularly limited. Generally, the compounds can be orally or parenterally (e.g. intravenously) administered approximately once a day in an amount of about 10 mg to 1,000 mg/day to an adult (average weight of 60 kg). The administration form can include, for example, powder, parvule, granule, tablet, capsule, injection or the like. In addition, the preparation can be made by using a conventional carrier or diluent according to conventional methods.

PREFERRED EMBODIMENTS OF THE INVENTION

This invention will be described concretely by the following experimental examples, but it is by no means restricted by these experimental examples unless exceeding the gist thereof.

Preparation examples of the compounds of this invention and physical and chemical properties thereof are as follows. Furthermore, measurement of NMR is made by using tetramethyl silane as an internal standard and the result is represented as ppm. "Part" in the examples shows part by volume.

EXPERIMENTAL EXAMPLE 1

1-(diphenylmethyl)piperazine (10.0 g) was dissolved in acetonitrile (50 ml) and sodium carbonate (6.5 g) and epibromohydrin (6.8 g) were added thereto and heated at reflux for 2.5 hours. After the resultant salt was filtered, the filtrate was concentrated under reduced pressure. The residue was purified by silica gel column chromatography (Waco Gel C-200, 200 g) and eluted with a mixed solvent of chloroform (99 parts)+methanol (1 part) to give 1-(diphenylmethyl)-4-(1-(2,3-epoxy) propyl)piperazine (5.9 g).

Nuclear Magnetic Resonance Spectrum

1H-NMR(CDC13, 500 MHz)δ: 2.30–2.80 (12H, m), 3.06– 3.10 (1H, m), 4.23 (1H, s), 7.16 (2H, t, J=7.3 Hz), 7.25 (4H, t, J=7.3 Hz), 7.40 (4H, d, J=7.3 Hz).

EXPERIMENTAL EXAMPLE 2

1,2,3,4-tetrahydroisoquinoline (25.0 g) was dissolved in acetonitrile (100 ml) and sodium carbonate (40.0 g) and epibromohydrin (31.0 g) were added thereto and heated at reflux for 4 hours. After the resultant salt was filtered, the filtrate was concentrated under reduced pressure. The residue was purified by silica gel column chromatography (Waco Gel C-200, 500 g) and eluted with a mixed solvent of chloroform (99 parts)+methanol (1 part) to give 2-[1-(2,3-epoxy)propyl]-1,2,3,4-tetrahydroisoquinoline (15.6 g).

Nuclear Magnetic Resonance Spectrum

1H-NMR(CDC13, 100 MHz)δ: 2.36–2.60 (2H, m), 2.73–3.03 (6H, m), 3.09–3.29 (1H, m), 3.65 (1H, d, J=14.9 Hz), 3.83 (1H, d, J=14.9 Hz), 6.94–7.20 (4H, m).

EXPERIMENTAL EXAMPLE 3

1-(diphenylmethyl)-4-(1-(2,3-epoxy)propyl)piperazine (3.0 g) and 4-(4-chlorophenyl)-4-hydroxypiperidine (2.5 g) were dissolved in o-dichlorobenzene (20 ml) and heated at reflux for 2.5 hours. After standing to cool, the product was purified by silica gel column chromatography (Waco Gel C-200, 100 g) to give 1-[1-(4-diphenylmethyl) piperazinyl]-3-[1-[4-(4-chlorophenyl)-4-hydroxy) piperidinyl]-2-propanol (compound ①, 4.6 g).

Infrared Absorption Spectrum

IRνmax (cm-1) KBr: 3300, 2950, 2650, 1620, 1450, 1100, 910, 830, 750, 710 (for hydrochloride).

Nuclear Magnetic Resonance Spectrum

1H-NMR(CDCl3, 500 MHz)δ: 1.50–1.90 (4H, m), 2.01–2.21 (2H, m), 2.30–2.55 (10H, m), 2.80–2.90 (2H, m), 3.87–3.93 (1H, m), 4.22 (1H, s), 7.16 (2H, t, J=7.3 Hz), 7.26 (4H, t, J=7.3 Hz), 7.30 (2H, d, J=8.5Hz), 7.40 (4H, d, J=7.3 Hz), 7.42 (2H, d, J=8.5 Hz).

FD Mass Spectrum

FD-MS (m/z): 519, 521 (M+).

EXPERIMENTAL EXAMPLE 4

2-[1-(2,3-epoxy)propyl]-1,2,3,4-tetrahydroisoquinoline (3.0 g) and 1-(diphenylmethyl)piperazine (4.4 g) were dissolved in o-dichlorobenzene (20 ml) and heated at reflux for 2.5 hours. After standing to cool, the product was purified by silica gel column chromatography (Waco Gel C-200, 150 g) to give 1-[2-(1,2,3,4-tetrahydro) isoquinolinyl]-3-[1-(4-diphenylmethyl)-piperazinyl]-2-propanol (compound ②, 6.0 g).

Infrared Absorption Spectrum

IRνmax (cm-1) KBr: 3400, 3000, 2550, 1620, 1450, 1080, 920, 760, 710 (for hydrochloride).

Nuclear Magnetic Resonance Spectrum

1H-NMR(CDCl3, 100 MHz)δ: 2.30–2.60 (12H, m), 2.75–2.95 (4H, m), 3.62–3.80 (2H, m), 3.92–4.03 (1H, m), 4.21 (1H, s), 7.00–7.51 (14H, m).

FD Mass Spectrum

FD-MS (m/z): 441 (M+).

PHARMACOLOGICAL TEST

Test Procedure (1)

The heart from a male rat weighing 300 to 380 g was isolated and perfusion was made under water-gauge pressure of 80 cm according to Langendorff's method. A Krebs-Henseleit bicarbonate solution (37° C., pH 7.4) containing 11 mM glucose, oxygenated with a mixed gas of 95% $O_2$+5% $CO_2$. Furthermore, the heart was compulsively driven by electrostimulation at 330 beats/min. After stabilizing for 10 minutes, perfusion was made for 10 minutes using the Krebs-Henseleit solution containing 5.5 mM calcium as calcium setting in which an amount of the test compound was dissolved. Thereafter, 1.5 ml of an aqueous solution containing 0.1 mg of adrenaline was added into the perfusate as a trigger drug, and after 1 minute, 1 ml of an aqueous solution containing 10 mg caffeine was added therein. After a further 2 minutes, the heart was taken out to be put in a formaldehyde solution. The heart was fixed in the formaldehyde solution and then was cut horizontally at intervals of about 3 mm. Each of the cut blocks was dehydrated, degreased and embedded in parrafin, in due form, and then was sliced into a 3 to 4 μm thickness. The cut sample was stained by Heidenhain's iron hematoxylin stain method to make a preparation. With an optical microscope, a five-rating evaluation (−, ±, +, ++, +++) was made on the basis of the degree of myocardial necrosis. Where the ration of myocardial necrosis to the sectional area of the left ventricle of the heart is not more than 5%, i.e. (−) and (±), it was determined that there was a myocardial necrosis inhibiting effect.

Test Procedure (2)

The heart from a male rat weighing 300 to 380 g was isolated and perfusion was made under water-gauge pressure of 80 cm according to Langendorff's method, under the same conditions as in Test Procedure (1). A latex balloon was inserted in the left ventricle of the heart and used to measure both left ventricular pressure and heart rate. In this test, when the heart function had stabilized, perfusion was made for 10 minutes using the perfusate containing the compound to be tested, and change in the heart function was recorded. The value of heart rate (HR)×left ventricular pressure (LVP) was evaluated as an indication of heart function.

TEST RESULT

Results of the Test Procedure (1) and (2) are shown in Table 1.

It can be seen from the column showing Degree of Myocardial Necrosis in Table 1 that Compounds ① and ② have a more potent effect of inhibiting myocardial tissue necrosis than does diltiazen hydrochloride (trade name: HERBESSER). In addition, as can be seen from the column showing Effect on Heart Function in Table 1, even in doses large enough to inhibit myocardial necrosis Compounds ① and ② have little effect on the heart, and as the effective ingredient of drugs for myocardial protection, are effective in the inhibition and prevention of myocardial necrosis and the treatment and prevention of acute myocardial infarction.

TABLE 1

| Effect on Heart Function in Table 1. | | | | |
|---|---|---|---|---|
| Compounds to be tested | Concentration (M) | Case Numbers | Degree of Myocardial Necrosis | Effect on Heart Function (HR × LVP, Control = 100%) |
| Physiological Saline | | 11 | +~++ | 100.2 ± 5.4 |
| Diltiazem Hydrochloride | $10^{-7}$ | 5 | +~++ | 68.3 ± 7.4* |
| Diltiazem Hydrochloride | $10^{-6}$ | 3 | +~++ | 35.9 ± 9.8* |
| Diltiazem Hydrochloride | $10^{-5}$ | 5 | ± | 10.4 ± 5.2* |
| Compound ① | $10^{-7}$ | 4 | ± | 96.8 ± 4.2 |
| Compound ① | $10^{-6}$ | 3 | −~+ | 93.6 ± 3.8 |
| Compound ② | $10^{-7}$ | 4 | − | 90.7 ± 4.8 |

Average Value ± Standard Deviation
*$P < 0.05$ (To Physiological Saline Injected Group)

INDUSTRIAL AVAILABILITY

The compounds of this invention are novel diphenylmethyl piperazine derivatives having the effect of inhibiting overcontraction and overextension of the myocardium and protecting against myocardial necrosis without being accompanied by a cardiodepressant effect. As medicinal drugs, for example, the compounds are far more effective in the treatment and prevention of acute myocardial infarction than previous drugs for the treatment and prevention thereof, and provide an excellent myocardial necrosis inhibitor which is effective in the inhibition and prevention of myocardial necrosis.

We claim:

1. A diphenylmethyl piperazine derivative represented by the following Formula [I]:

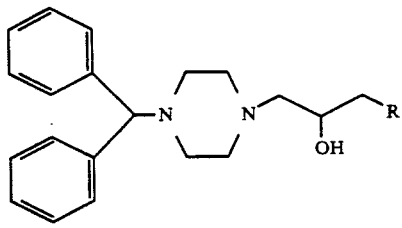

wherein R represents

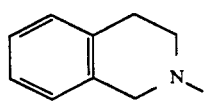 or 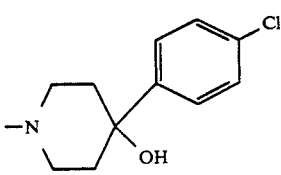

or a pharmaceutically acceptable salt thereof.

2. A pharmaceutical composition for inhibiting myocardial necrosis which comprises a mycardial necrosis-inhibiting effective amount of diphenylmethyl piperazine having the formula:

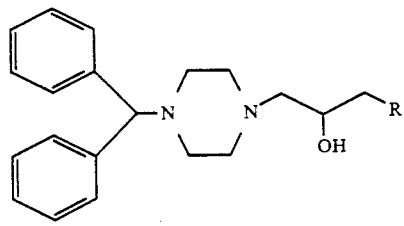

wherein R represents

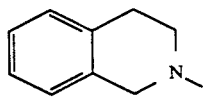

or

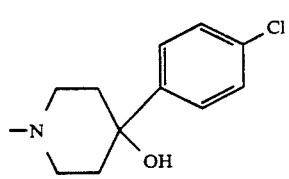

or a pharmaceutically acceptable salt thereof and a pharmaceutical carrier thereof.

3. A pharmaceutical composition for the treatment of acute myocardial infarction which comprises an effective amount for said treatment of a diphenylmethyl piperazine having the following formula:

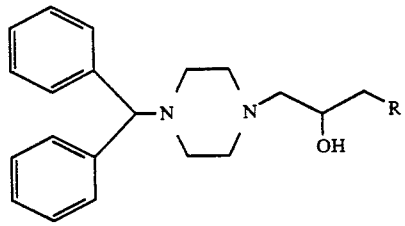

wherein R represents

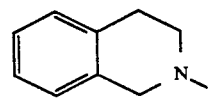

or

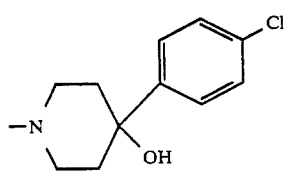

or a pharmaceutically acceptable salt thereof and a pharmaceutical carrier therefor.

4. The diphenylmethyl piperazine as defined in claim 1, wherein R represents

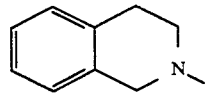

5. The diphenylmethyl piperazine as defined in claim 1, wherein R represents

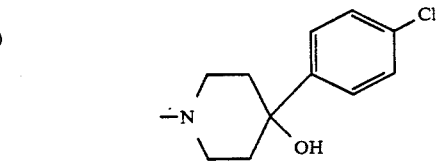

6. The pharmaceutical composition as defined in claim 2, wherein R represents

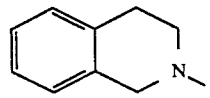

7. The pharmaceutical composition as defined in claim 2, wherein R represents

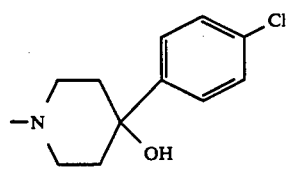

8. The pharmaceutical composition as defined in claim 3, wherein R represents

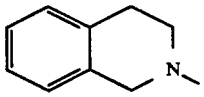

9. The pharmaceutical composition as defined in claim 3, wherein R represents

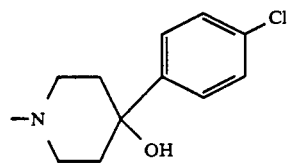

10. A method for inhibiting myocardial necrosis in an animal in need of such treatment which comprises administrating to said animal a myocardial necrosis inhibiting effective amount of a compound according to claim 1, having the formula

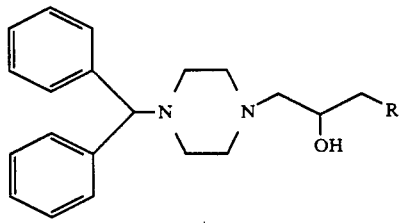

wherein R represents

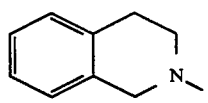

or

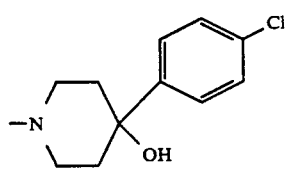

or a pharmaceutically acceptable salt thereof.
11. The method, according to claim 10, wherein R is

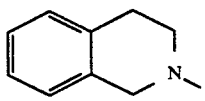

12. The method, according to claim 10, wherein R is

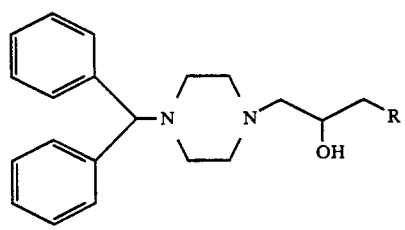

13. A method for the treatment of acute myocardial infarction in an animal in need of said treatment which comprises administrating to said animal an effective amount of a compound according to claim 1, having the formula

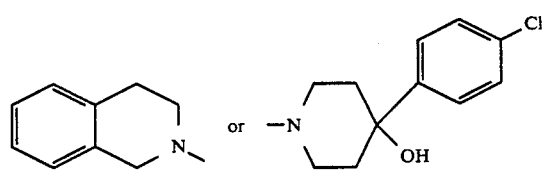

wherein R represents

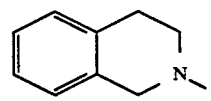 or 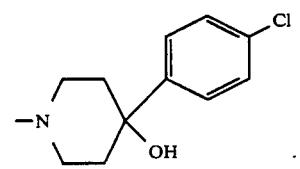

or a pharmaceutically acceptable salt thereof.
14. The method, according to claim 13, wherein R is

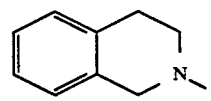

15. The method, according to claim 13, wherein R is

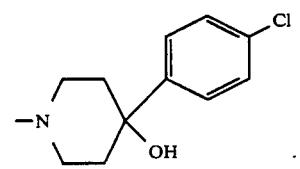

* * * * *

UNITED STATES PATENT AND TRADEMARK OFFICE
CERTIFICATE OF CORRECTION

PATENT NO. : 5,304,558
DATED : April 19, 1994
INVENTOR(S) : Noboru Kaneko, et al.

It is certified that error appears in the above-indentified patent and that said Letters Patent is hereby corrected as shown below:

Column 3, line 18: after "for" insert
--example, inorganic acid salts such as hydrochloride,--
Column 9, line 29, Claim 2: "mycardial"
should read --myocardial--

Signed and Sealed this

Fourteenth Day of February, 1995

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO.  : 5,304,558
DATED       : April 19, 1994
INVENTOR(S) : Noboru Kaneko, et al.

It is certified that error appears in the above-indentified patent and that said Letters Patent is hereby corrected as shown below:

On the Title Page, Section [73]: "Kirin Brewery Co., Ltd., Tokyo, Japan" should read --Noboru Kaneko, Tokyo, Japan--

Signed and Sealed this

Twenty-fourth Day of October, 1995

Attest:

BRUCE LEHMAN

*Attesting Officer*    *Commissioner of Patents and Trademarks*